United States Patent [19]
Phillips

[11] 3,944,557
[45] Mar. 16, 1976

[54] PYRIDINIUM SALTS
[75] Inventor: John Norbert Phillips, Yarralumla, Australia
[73] Assignee: Commonwealth Scientific & Industrial Research Organization, Canberra, Australia
[22] Filed: Sept. 11, 1973
[21] Appl. No.: 396,297

[52] U.S. Cl. 260/294.9; 260/294.8 E; 260/294.8 R; 424/263
[51] Int. Cl.$^2$................................ C07D 213/60
[58] Field of Search .... 260/294.9, 294.8 E, 294.8 R

[56] References Cited
OTHER PUBLICATIONS
Little et al., *J. American Chem. Soc.* Vol. 80, pp. 2832 to 2838 (1958); Carboni et al., *J. Am. Chem. Soc.* Vol. 80, pp. 2838 to 2840 (1958) (note p. 2839 in particular)

*Primary Examiner*—John D. Randolph
*Attorney, Agent, or Firm*—Cushman, Darby & Cushman

[57] ABSTRACT

The compounds of the invention are of the class of 2-amino-4-substituted amino-5-cyano pyridinium salts, useful as fungicidal agents. The preparation of these salts by reaction of an N-substituted cyano acetamide with a phosphorous halide or oxyhalide is described.

8 Claims, No Drawings

PYRIDINIUM SALTS

This invention relates to novel pyridinium salts which exhibit useful fungicidal properties, to methods for the preparation of these salts, and to methods and compositions for controlling the growth of fungi.

In particular, the present invention relates to novel pyridinium salts of the general formula I;

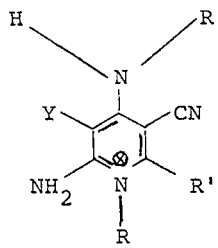 (I)

wherein
Y is selected from the group consisting of hydrogen and halogen, particularly chlorine or bromine;
R is selected from the group consisting of straight- or branched-chain, substituted or unsubstituted alkyl, particularly an alkyl group of one to twelve carbon atoms and more particularly an alkyl group of five to ten carbon atoms; substituted or unsubstituted cycloalkyl, particularly a cycloalkyl group of five to ten carbon atoms; and aralkyl, particularly a benzyl or phenethyl group;
R' is selected from the group consisting of hydrogen, halogen, particularly a chlorine or bromine atom; sulphonate; azido; radicals of the formula —N-H—$SO_2$—$R_1$, wherein $R_1$ represents a substituted or unsubstituted aryl group or a straight or branched-chain, substituted or unsubstituted alkyl group; radicals of the formula

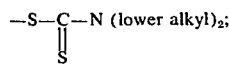

radicals of the formula —CH(CN)—$R_2$ wherein $R_2$ represents —COOH, —COO— (lower alkyl) or —NH—CO—$NH_2$; and radicals of the formulae

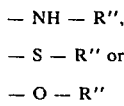

wherein
R'' represents hydrogen, substituted or unsubstituted, straight- or branched-chain alkyl, alkenyl or alkynyl, substituted or unsubstituted aryl or aralkyl or cyano;
and $A^-$ represents an anion, particularly a chloride or bromide ion.

Typical substituents which may be introduced in the alkyl, alkenyl, alkynyl, cycloalkyl, aryl or aralkyl groups include halo radicals, particularly chloro or bromo radicals, and nitro, lower-alkoxy, pyridyl, carboxyl or furyl radicals.

It will be apparent that when R' represents a sulphonate radical (—$SO_3^-$) in the above general formula, the anion $A^-$ will not be present.

It will be apparent to persons skilled in this art that by removal of a proton from the compounds of general formula I, an imine conjugate base Ia will be formed.

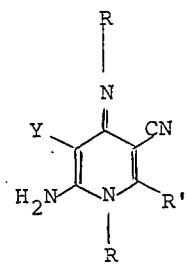 Ia

It will also be apparent that where R' represents a radical of the formula —XH in which X represents —S— or —O—, removal of a proton will also form a base Ib as set out below.

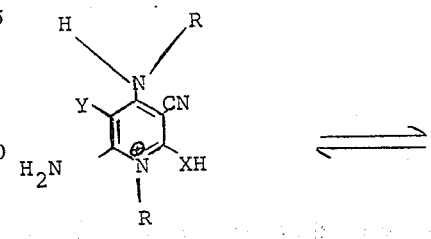

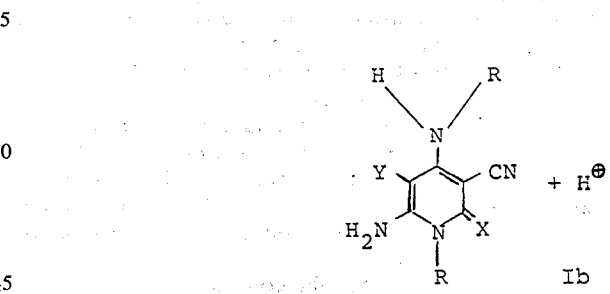

Since these compounds may be used either in the form of the salt or in the form of the base, references herein to compounds of the general formula I are to be understood as references to those compounds either as the salt or as the base.

As typical compounds of the general formula I, there may be mentioned those in which Y represents a hydrogen atom, R' represents a chlorine atom and R represents n- or iso-butyl, n-hexyl, cyclohexyl, n-heptyl, n-octyl or n-nonyl; and those in which Y represents a bromine atom, R' represents a chlorine atom and R represents n-hexyl or n-octyl. Other typical compounds are set out in the Examples below.

The compounds of this invention in which Y represents a hydrogen atom, R' represents a halogen atom and R is as defined above may be prepared by the reaction of an N-substituted cyanoacetamide of the formula II with a phosphorous halide or oxyhalide under known reaction conditions to form a compound of formula III:

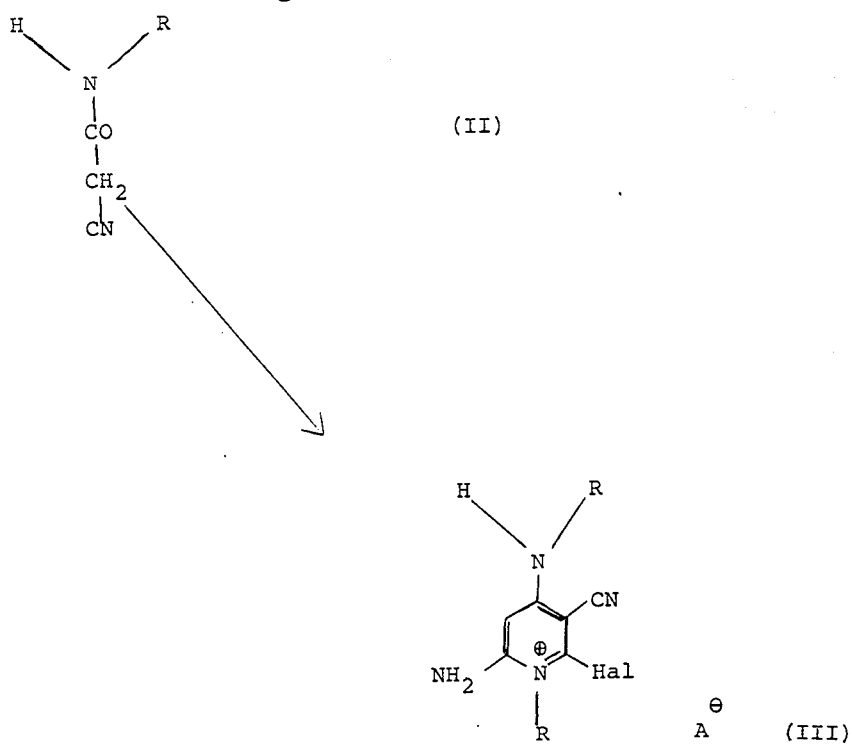

In a typical procedure, the N-substituted cyanoacetamide is dissolved in an organic solvent such as chloroform and phosphorous oxychloride added to the solution. The reaction mixture is then warmed on a steam bath under reflux for about two hours and the product collected and recrystallised.

The compounds of the formula III may then be halogenated in the 3-position and/or the 6-halo substituent replaced by other radicals represented by R' using known techniques to form the other compounds of the general formula I. Typical procedures are illustrated in the Examples below.

It has been found that the compounds of this invention show a range of anti-fungal activity and the typical compounds mentioned above have been found to completely inhibit spore germination in *Monolinia fructicola* at 1 – 100 ppm, to control *Phytophthora cinnamomi* infection of lupin seedlings at 1 – 8 ppm and to prevent infection of tomato seedlings by *Fusarium oxysporum* and cotton seedlings by *Rhizoctonia solani* when incorporated in the soil at 8 kg/ha.

In another aspect, this invention therefore provides a method of controlling fungal infection of plants which comprises treating the fungi, the plants, the soil or the plant seeds with an effective amount of a compound of formula I.

The amount of the compound of general formula I necessary to achieve the desired control in carrying out the above methods may be readily determined by simple experimentation and, by way of example, amounts of particular compounds within this general formula which may be used to control growth of fungi have been mentioned above.

In accordance with a further aspect of this invention there are provided compositions for controlling the growth of fungi which comprise an inert carrier and an effective amount of a compound of the general formula I. The compositions according to this aspect may be either liquid or solid as desired. The precise formulation employed may be varied according to the manner in which it is to be applied, the extent of control desired or necessary and the particular type of fungi to be controlled. The most advantageous composition for the control of a specific fungi may be readily determined by persons of ordinary skill in the art by routine experimentations in accordance with the teaching of this invention and the various factors set out above.

The compositions may be formulated with solid inert carriers, such as finely divided talc or silica to give powder compositions or vermiculites or the like to give granular compositions. Alternatively, liquid inert carriers may be used, such as vegetable or mineral oils, to provide spray compositions. In addition to the compound of general formula Ia and inert carrier, the compositions according to this invention may include other active components to assist the formulation and use of the compositions, such as emulsifying, dispersing and wetting agents.

One example of the manner in which the compounds of the present invention may be used is by formulation into a composition for spraying cotton plants prior to harvesting. A compound of the present invention is incorporated into a known spray composition which also includes a defoliating agent and the composition containing both active agents is sprayed onto the cotton plants to provide fungicidal protection at the same time as the plants are defoliated.

The following Examples set forth procedures for the preparation of the compounds of this invention and illustrate, but in no way limit, the present invention.

EXAMPLE I

N-methyl cyanoacetamide (9.8., 0.1 mole) was dissolved in chloroform (50 ml) and phosphorous oxychloride (15.3 g., 0.1 mole) added. The reaction mixture was warmed on a steam bath under reflux for 2 hours during which time the product, 2-amino-6-chloro-5-cyano-1-methyl-4-methylamino pyridinium chloride (compound 1 - table 1) crystallized. It was collected and recrystallized from methanol to give a pale yellow solid (9.4g., 80%) [m.p. 250°C, C 41.51 (41.21); H 4.26 (4.32); N 24.11 (24.03); Cl 30.3 (30.4)]

Higher homologues in the series were soluble in chloroform and were isolated by removal of the solvent in vacuo and treatment of the residue with cold methanol.

Other compounds of formula III, in which Hal represents chlorine and R is as set out in Table 1 below, were prepared in a similar manner.

Examples 2 to 6 illustrate halogenation of compounds of formula III in the 3-position and substitution in the 6-position.

EXAMPLE 2

3.37 gms (.01 mole) of 2-amino-6-chloro-5-cyano-1-n-hexyl-4-n-hexylamino pyridinium chloride (compound II - Table 1) was dissolved in methanol and 1.0 gm (0.01 mole) of triethylamine and 0.8 gms (0.011 mole) of n-butylamine added. The solution was refluxed for 1 hour and on cooling 2.5 gms (60% yield) of 2-amino-6-n-butylamino-5-cyano-1-n-hexyl-4-n-hexylamino pyridinium chloride (compound 42 - Table 2) crystallised out. [m.p. 179° – 180°C. c 64.88 (64.6) H 9.81 (9.78) N17.11 (17.1)].

Other derivatives prepared in a similar manner using different pyridinium salts and a variety of amines and amides are listed in Table 2.

EXAMPLE 3

3.2 gms (.01 mole) of 2-amino-1-n-butyl-4-n-butylamino-60chloro-5-cyano-pyridinium chloride (compound 6 - Table 1) was dissolved in hot water and 1.5 gms (0.012 moles) of sodium sulphite added. One cooling 2.8 gms (85% yield) of 2-amino-1-n-butyl-4-n-butylamino-5-cyano-pyridinium betaine-6-sulphonate (compound 60 - Table 3) crystallised out and was filtered off. [MPt 240° – 245°C with decomposition. C 51.31 (51.51) H 6.76 (6.79) N 16.70 (17.17) S 9.9 (9.8) ].

Other derivatives prepared in a similar manner (aqueous alcohol could be used in the case of less water soluble starting materials) are listed in Table 3.

EXAMPLE 4

4.85 gms (.01 mole) of 2-amino-6-chloro-5-cyano-1-n-decyl-4-n-decylamino pyridinium chloride (compound 16 - Table 1) was suspended in water and 1.8 gms (0.012 mole) bromine added to the rapidly stirred suspension which was heated on a water bath for 30 minutes. On cooling 4.5 gms (75% yield) of 2-amino-3-bromo-6-chloro-5-cyano-1-n-decyl-4-n-decylamino pyridinium bromide (compound 70 Table 4) was filtered off and recrystallised from ethanol. [MPt 166° – 168°C. c 51.62 (51.27) H 7.31 (7.40) N 9.20 (9.20)].

Other derivatives prepared similarly are listed in Table 4.

EXAMPLE 5 a. 2.3 gms (.01 mole) of 2-amino-6-chloro-5-cyano-1-methyl-4-methylamino pyridinium chloride (compound 1 - Table 1) was dissolved in water and 0.92 gms (.01 mole) of thioglycollic acid and 2.0 gms (0.02 mole) of triethylamine added. After 30 minutes 1.5 gms (60% yield) of 2-amino-5-cyano-1-methyl-4-methylamino-pyridinium-betaine-6-thioglycollate (compound 74 - Table 5) was filtered off (MPt>240°C).

b. 3.15 gms (0.01 mole) of 2-amino-1-n-butyl-4-n-butylamino-6-chloro-5-cyano pyridinium chloride (compound 6 - Table 1), 1.24 gms (0.01 mole) of benzyl mercaptan and 1.0 gm (0.01 mole) of triethylamine was dissolved in dimethylformamide and heated at 100°C for 1 hour. The dimethylformamide was evaporated off, ethanol added and 2.0 gms (50% yield) of 2-amino-6-benzylmercapto-1-n-butyl-4-n-butylamino-5-cyano pyridinium chloride (compound 75 - Table 5) crystallised out and was recrystallised from ethanol (MPt 145° – 147°C).

c. 4.5 gms (.01 mole) of 2-amino-6-chloro-5-cyano-1-n-octyl-4-n-octylamino pyridinium chloride (compound 14 - Table 1) was dissolved in dimethylformamide and 2.2 gms (0.01 mole) of sodium diethyldithiocarbamate added and the solution refluxed for 60 minutes. This was then cooled, filtered and the solvent evaporated off. Methanol was added and 1.6 gms (30% yield) of 2-amino-5-cyano-6-diethylthiocarbamylthio-1-n-octyl-4-n-octylamino pyridinium chloride (compound 80 - Table 5) was filtered off and recrystallised from methanol (MPt 124° – 126°C.)

d. 3.7 gms (.01 ml) of 2-amino-6-chloro-5-cyano-1-n-hexyl-4-n-hexylamino pyridinium chloride (compound 11 - Table 1) was dissolved in ethanol and 1.1 gm (.01 mole) thiophenol and 1.0 gm (0.01 mole) of triethylamine added. The solution was left 16 hours at room temperature poured into iced water and 2.3 gms (50% yield) of 2-amino-5-cyano-1-n-hexyl-4-n-hexylamino-6-phenylmercapto pyridinium chloride (compound 78 - Table 5) filtered off (MPt 227° –228°C).

Analogous compounds prepared by similar methods to those described in examples 5(a) (b) (c) and (d) are listed in Table 5.

EXAMPLE 6 a. 3.2 gms (.01 mole) of 2-amino-1-n-butyl-4-n-butylamino-6-chloro-5-cyano-pyridinium chloride (compound 6 - Table 1) was dissolved in hot water, 4.0 gms (0.04 mole) of triethylamine added and the solution refluxed on a boiling water bath. After 2 hours 2.0 gms (75% yield) of 2-amino-1-n-butyl-4-n-butylamino-5-cyano-pyridine-6-one (compound 87 - Table 6) had precipitated and was filtered off. (MPt 177° – 179°C).

b. 2.6 gms (.01 mole) of 2-amino-6-chloro-5-cyano-10ethyl-4-ethylamino pyridinium chloride (compound 2 - Table 1) was dissolved in water and (.03 mole) of sodium sulphide added. 2.0 gms (90% yield) of 2-amino-5-cyano-1-ethyl-4-ethylamino pyridine-6-thione (compound 85 - Table 6) immediately precipitated and was filtered off. (MPt 190° – 192°C).

c. 2.3 gms (.01 mole) of 2-amino-6-chloro-5-cyano-1-methyl-4-methylamino pyridinium chloride (compound 1 - Table 1) was dissolved in water and 0.66 gms (.01 mole) of malononitrile and 2.0 gms (.02 mole) of triethylamine added. After a few minutes 1.7 gms (75% yield of 2-amino-5-cyano-1-methyl-4-methylamino-6-dicyanomethyl pyridinium chloride (compound 83 - Table 6) (MPt>240°C) crystallised out.

A number of analogous conjugate bases prepared according to the method described in (a) (b) and (c) above are listed in Table 6.

EXAMPLE 7

0.8 gms (.012 mole) of sodium azide was added to an aqueous solution containing 2.6 gms (.01 mole) of 2-amino-6-chloro-5-cyano-1-ethyl-4-ethylamino pyridinium chloride (compound 2 - Table 1) left for 2 hours at room temperature and then cooled. 2.0 gms (70% yield) of 2-amino-6-azido-5-cyano-1-ethyl-4-ethylamino pyridinium chloride crystallised out (MPt 164° – 165°C).

EXAMPLE 8

3.2 gms (.01 mole) of 2-amino-1-n-butyl-4-n-butylamino-6-chloro-5-cyano-pyridinium chloride (compound 6 - Table 1) was dissolved in dry dimethylformamide, 0.06 gms (0.01 mole) of sodium methoxide added, and the mixture refluxed for 60 minutes, filtered and solvent evaporated off. The solid was recrystallised from acetone to give 1.0 gm (30% yield) of 2-amino-1-n-butyl-4-n-butylamino-5-cyano-6-methoxy pyridinium chloride (MPt 187° – 189°C.)

TABLE 1

Compounds of the formula:

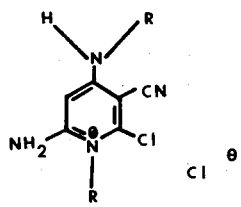

prepared as in Example I

| Product: Compound No. | R | % Yield | MPt (°C) | ANALYSIS C | H | N | Cl |
|---|---|---|---|---|---|---|---|
| 1 | Methyl | 80 | 250 | 41.51 (41.21) | 4.26 (4.32) | 24.11 (24.03) | 30.3 (30.4) |
| 2 | ethyl | 80 | >250 | | | | |
| 3 | n-propyl | 75 | 215–217 | | | | |
| 4 | isopropyl | 40 | 196–197 | 49.89 (49.81) | 6.51 (6.27) | 19.25 (19.37) | |
| 5 | alkyl | 60 | 192–194 | | | | |
| 6 | n-butyl | 85 | 230–231 | 52.88 (53.16) | 6.94 (7.01) | 17.99 (17.71) | 22.7 (22.4) |
| 7 | isobutyl | 50 | 237–239 | | | | |
| 8 | sec-butyl | 30 | 177–178 | 52.73 (53.16) | 7.06 (7.01) | 17.61 (17.71) | |
| 9 | n-pentyl | 80 | 238–240 | | | | |
| 10 | cyclopentyl | 70 | 205–207 | 56.44 (56.29) | 6.46 (6.49) | 16.40 (16.41) | 21.0 (20.8) |
| 11 | n-hexyl | 75 | 202–204 | 58.21 (57.90) | 7.80 (8.04) | 15.16 (15.00) | 18.8 (19.0) |
| 12 | cyclohexyl | 60 | 213–214 | 58.51 (58.53) | 6.97 (7.10) | 15.26 (15.17) | 18.8 (19.2) |
| 13 | n-heptyl | 80 | 238–240 | | | | |
| 14 | n-octyl | 75 | 233–234 | 61.85 (61.52) | 8.93 (8.91) | 13.07 (13.04) | 16.4 (16.5) |
| 15 | n-nonyl | 75 | 230–232 | 63.2 (63.3) | 9.19 (9.20) | 12.25 (12.40) | 15.5 (15.3) |
| 16 | n-decyl | 75 | 226–228 | 64.3 (64.7) | 9.48 (9.69) | 11.54 (11.78) | 14.6 (14.3) |
| 17 | benzyl | 60 | 192–194 | 62.09 (62.34) | 5.01 (4.67) | 14.79 (14.55) | 18.1 (18.4) |
| 18 | phenylethyl | 50 | >240 | | | | |

TABLE 2

Compounds of the formula:

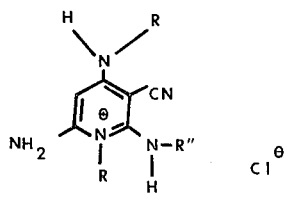

prepared as in Example 2.

| Starting Compound No. | Reactant | R | R'' | Product Compound No. | % Yield | MPt(°C) |
|---|---|---|---|---|---|---|
| 1 | ammonia | methyl | H | 19 | 70 | >240 |
| 1 | cyanamide | methyl | cyano | 20 | 20 | >240 |
| 1 | N-propylamine | methyl | n-propyl | 21 | 80 | >240 |
| 1 | allylamine | methyl | allyl | 22 | 70 | >240 |
| 1 | furfurylamine | methyl | furfuryl | 23 | 60 | >240 |
| 1 | benzylamine | methyl | benzyl | 24 | 80 | >240 |
| 1 | p-toluenesulphonamide | methyl | p-toluenesulphonyl | 25 | 90 | >240 |
| 1 | n-octylamine | methyl | n-octyl | 26 | 60 | 203–205 |
| 1 | n-dodecylamine | methyl | n-dodecyl | 27 | 80 | 210–214 |
| 1 | glycine | methyl | carboxymethyl | 28 | 80 | >240 |
| 2 | 2-bromoethylamine | ethyl | 2-bromoethyl | 29 | 80 | >240 |
| 2 | furfurylamine | ethyl | furfuryl | 30 | 80 | >240 |
| 2 | 2-picolylamine | ethyl | 2-picolyl | 31 | 75 | 233–234 |
| 3 | furfurylamine | n-propyl | furfuryl | 32 | 75 | 225 |
| 4 | n-butylamine | isopropyl | n-butyl | 33 | 85 | 188–190 |
| 4 | furfurylamine | isopropyl | furfuryl | 34 | 85 | 202 |
| 6 | n-butylamine | n-butyl | n-butyl | 35 | 80 | 224 |
| 6 | furfurylamine | n-butyl | furfuryl | 36 | 80 | 248 |
| 6 | n-octylamine | n-butyl | n-octyl | 37 | 60 | 228–229 |
| 6 | glycine | n-butyl | carboxymethyl | 38 | 80 | >240 |
| 10 | cyanamide | cyclopentyl | cyano | 39 | 70 | >240 |
| 11 | methylamine | n-hexyl | methyl | 40 | 30 | 228–230 |
| 11 | furfurlamine | n-hexyl | furfuryl | 41 | 50 | >240 |
| 11 | n-butylamine | n-hexyl | n-butyl | 42 | 60 | 179–180 |
| 11 | n-hexylamine | n-hexyl | n-hexyl | 43 | 70 | 159–160 |
| 11 | n-octylamine | n-hexyl | n-octyl | 44 | 50 | 148–151 |
| 12 | methylamine | cyclohexyl | methyl | 45 | 60 | 205–207 |
| 14 | ammonia | n-octyl | H | 46 | 90 | 231–233 |
| 14 | methylamine | n-octyl | methyl | 47 | 80 | 156 |
| 14 | cyanamide | n-octyl | cyano | 48 | 90 | 226 |
| 14 | ethylamine | n-octyl | ethyl | 49 | 80 | 209–211 |
| 14 | n-propylamine | n-octyl | n-propyl | 50 | 80 | 170–172 |
| 14 | n-butylamine | n-octyl | n-butyl | 51 | 80 | 158–160 |
| 14 | furfurylamine | n-octyl | furfuryl | 52 | 50 | 192–194 |
| 14 | n-hexylamine | n-octyl | n-hexyl | 53 | 60 | 140–142 |
| 14 | n-octylamine | n-octyl | n-octyl | 54 | 50 | 154–156 |
| 16 | ammonia | n-decyl | H | 55 | 60 | 240 |
| 17 | cyanamide | benzyl | cyano | 56 | 80 | >240 |

TABLE 3

Compounds of the formula:

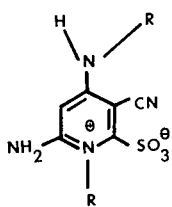

prepared as in Example 3.

| Starting Compound No. | R | Product Compound No. | % Yield | MPt(°C) | ANALYSIS C | H | N | S |
|---|---|---|---|---|---|---|---|---|
| 1 | methyl | 57 | 85 | >240 | 39.27 (39.67) | 4.26 (4.16) | 22.76 (23.13) | 13.0 (13.2) |
| 2 | ethyl | 58 | 80 | >240 | | | | |
| 4 | isopropyl | 59 | 80 | >240 | | | | |
| 6 | n-butyl | 60 | 80 | 240–245 | 51.31 (51.51) | 6.76 (6.79) | 16.70 (17.17) | 9.9 (9.8) |
| 7 | isobutyl | 61 | 90 | >240 | | | | |
| 12 | cyclohexyl | 62 | 60 | >240 | 56.95 (57.12) | 6.85 (6.92) | 14.61 (14.80) | 8.2 (8.5) |
| 14 | n-octyl | 63 | 80 | 240–241 | | | | |

TABLE 4

Compounds of the formula:

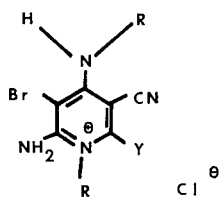

prepared as in Example 4.

| Starting Compound No. | R | Y | Product Compound No. | % Yield | MPt(°C) |
|---|---|---|---|---|---|
| 3 | n-propyl | chloro | 64 | 80 | 125–128 |
| 59 | iso-propyl | sulphonate | 65 | 60 | >240 |
| 6 | n-butyl | chloro | 66 | 60 | 178–180 |
| 11 | n-hexyl | chloro | 67 | 50 | 182–184 |
| 14 | n-octyl | chloro | 68 | 90 | 166–167 |
| 15 | n-nonyl | chloro | 69 | 70 | 169–171 |
| 16 | n-decyl | chloro | 70 | 75 | 166–168 |
| 17 | benzyl | chloro | 71 | 70 | 136–138 |
| 56 | benzyl | cyanamino | 72 | 80 | >240 |

TABLE 5

Compounds of the formula:

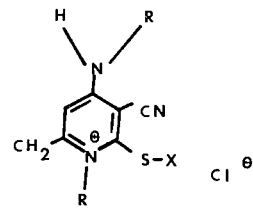

prepared as in Example 5

| Starting Compound No. | R | X | Product Compound No. | % Yield | MPt(°C) |
|---|---|---|---|---|---|
| 1 | methyl | benzyl | 73 | 40 | 145–147 |
| 1 | methyl | carboxymethyl | 74 | 80 | >240 |
| 6 | n-butyl | benzyl | 75 | 50 | 145–147 |
| 6 | n-butyl | carboxymethyl | 76 | 50 | >240 |
| 6 | n-butyl | dimethylthiocarbamoyl | 77 | 70 | 169–171 |
| 11 | n-hexyl | phenyl | 78 | 50 | 227–228 |
| 12 | cyclohexyl | phenyl | 79 | 50 | 227–229 |
| 14 | n-octyl | diethylthiocarbamoyl | 80 | 30 | 124–126 |

TABLE 6

Compounds of the formula:

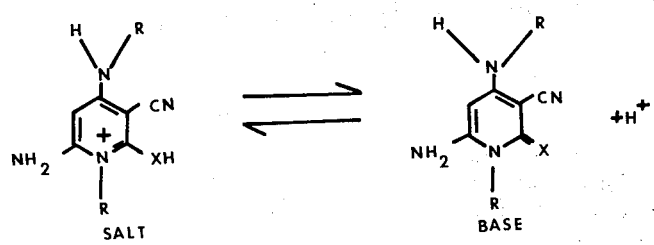

prepared as in Example 6.

| Starting Compound No. | R | XH | Product Compound No. | % Yield | MPt (°C) (Base form) |
|---|---|---|---|---|---|
| 1 | methyl | hydroxy | 81 | 80 | >240 |
| 1 | methyl | mercapto | 82 | 80 | >240 |
| 1 | methyl | dicyanomethyl | 83 | 75 | >240 |
| 1 | methyl | carboethoxy-cyanomethyl | 84 | 60 | >240 |
| 2 | ethyl | mercapto | 85 | 90 | 190–192 |
| 2 | ethyl | carboamido-cyanomethyl | 86 | 70 | 227–228 |
| 6 | n-butyl | hydroxy | 87 | 75 | 177–179 |
| 6 | n-butyl | mercapto | 88 | 80 | 173–175 |
| 11 | n-hexyl | mercapto | 89 | 70 | 103–104 |

The anti-fungal activity of typical compounds according to the present invention is illustrated in the results set out in Table 7 below.

TABLE 7

| Compound No. | Monolinia fructicolaspore germination | Phytophthora cinnamomi on lupin[2] | Rhizoctonia solani on cotton | Fusarium oxysporum on tomato[4] |
|---|---|---|---|---|
| 13 | ++ | ++ | – | + |
| 14 | ++ | ++ | ++ | + |
| 17 | + | + | – | + |
| 23 | – | – | – | ++ |
| 27 | – | 30 | ++ | – |
| 36 | + | + | + | – |
| 42 | ++ | ++ | – | – |
| 44 | ++ | ++ | – | + |
| 46 | ++ | ++ | + | – |
| 59 | – | – | ++ | – |
| 67 | ++ | + | – | + |
| 78 | ++ | ++ | + | – |

1. 50% inhibition of spore germination of *M. fructicola*
   $\leq 5$ ppm ++
   $>5 \leq 50$ ppm +
   $>50$ ppm –
2. Protection of lupin seedlings from infection by
   *P. cinnamomi*  $\leq 2$ ppm ++
   $>2 \leq 8$ ppm +
   $>8$ ppm –
3. Infection of cotton seedlings by *Rh. solani*
   100% protection at 16 kg/ha (soil application) ++
   50% protection at 16 kg/ha (soil application) +
4. Infection of tomato seedlings by *F. oxysporum*
   100% protection 8 kg/ha (soil application) ++
   50% protection at 8 kg/ha (soil application) +

We claim:
1. Compound of the formula:

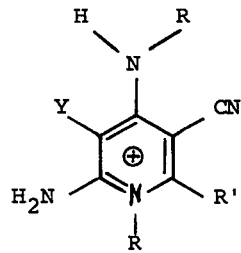

wherein:
Y is selected from the group consisting of hydrogen and halogen;
R is selected from the group consisting of straight or branched-chain alkyl or a chloro, bromo, nitro, lower alkoxy, pyridyl, carboxyl or furyl substituted alkyl of one to twelve carbon atoms; a cycloalkyl or a chloro, bromo, nitro, lower alkoxy, pyridyl, carboxyl or furyl substituted cycloalkyl of 5 to 10 carbon atoms; and aralkyl;
R' is selected from the group consisting of hydrogen; halogen; sulphonate; azido; radicals of the formula —NH—SO$_2$—R$_1$ wherein R$_1$ represents p-toluyl or a straight-or branched-chain alkyl or a chloro, bromo, nitro, lower alkoxy, pyridyl, carboxyl or furyl substituted alkyl of one to twelve carbon atoms or radicals of the formula

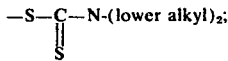

radicals of the formula —CH—(CN)—R₂, wherein R₂ represents —COOH, —COO (lower alkyl) or —NH—CO—NH₂; and radicals of the formulae —NH—R'', —S—R'' or —O—R'', wherein R'' represents hydrogen, a straight- or branched-chain alkyl or a chloro, bromo, nitro, lower alkoxy, pyridyl, carboxyl or furyl substituted alkyl of up to 12 carbon atoms, alkenyl of at least three carbon atoms or alkynyl, a phenyl, benzyl or cyano, furfuryl, carboxymethyl, 2-bromoethyl, 2-picolyl, dimethyl-thiocarbamoyl or diethylthiocarbamoyl; and A⁻ represents an anion.

2. A compound of the formula

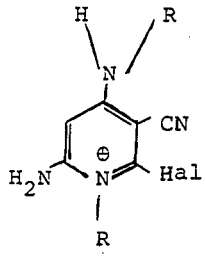

wherein
Hal represents halogen; and
R is as defined in claim 1.

3. The compound of the formula

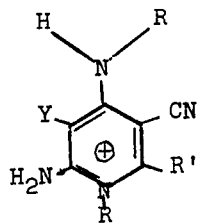

wherein
Y is hydrogen, R is n-octyl and R' is chloro.

4. The compound of claim 1, wherein R₁ is p-toluyl; wherein when R'' is alkyl, R'' is methyl, ethyl, n-propyl, n-butyl, n-hexyl, n-octyl or n-dodecyl andd wherein if R'' is alkenyl, then R'' is allyl.

5. A process for the preparation of a compound of the formula I

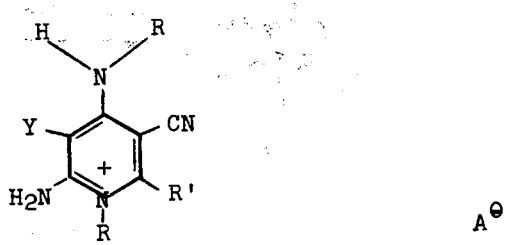

characterized in that a compound of the formula II

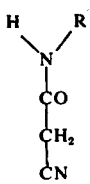

in which each of R, R' and Y is as defined in claim 1, is reacted with a phosphorous halide or phosphorous oxyhalide to produce a compound of the general formula III

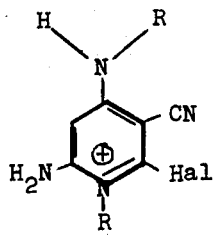

6. A process as claimed in claim 5, wherein the compound of formula II is dissolved in chloroform, the phosphorous halide or oxyhalide added to the solution and the mixture warmed under reflux.

7. The process of claim 5, which further includes the step of halogenating the compound of formula III in the 3-position.

8. The compound of claim 4, wherein when R is aralkyl, R is benzyl or phenylethyl.

* * * * *

UNITED STATES PATENT OFFICE
CERTIFICATE OF CORRECTION

Patent No. 3,944,557          Dated   March 16, 1976

Inventor(s)      John Norbert Phillips

It is certified that error appears in the above-identified patent and that said Letters Patent are hereby corrected as shown below:

In the heading:

Insert priority data as follows: --September 11, 1972

Australia No. PB0396--

In the claims:

Correct the formula in claim 1 as follows:

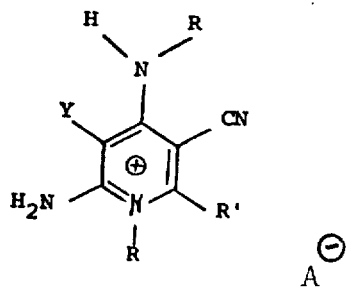

Claim 1, last line, "A" should read -- $A^{\ominus}$ --.

Signed and Sealed this

Twenty-first Day of September 1976

[SEAL]

Attest:

RUTH C. MASON
*Attesting Officer*

C. MARSHALL DANN
*Commissioner of Patents and Trademarks*